United States Patent
Carrascoso et al.

(10) Patent No.: US 10,837,970 B2
(45) Date of Patent: Nov. 17, 2020

(54) IDENTIFICATION AND USE OF GLYCOPEPTIDES AS BIOMARKERS FOR DIAGNOSIS AND TREATMENT MONITORING

(71) Applicant: Venn Biosciences Corporation, South San Francisco, CA (US)

(72) Inventors: Aldo Mario Eduardo Silva Carrascoso, Daly City, CA (US); Carolyn Ruth Bertozzi, Menlo Park, CA (US); Carlito Bangeles Lebrilla, Davis, CA (US); Lieza Marie Araullo Danan-Leon, S. San Francisco, CA (US)

(73) Assignee: Venn Biosciences Corporation, South San Francisco, CA (US)

( * ) Notice: Subject to any disclaimer, the term of this patent is extended or adjusted under 35 U.S.C. 154(b) by 127 days.

(21) Appl. No.: 16/120,016

(22) Filed: Aug. 31, 2018

(65) Prior Publication Data
US 2019/0101544 A1   Apr. 4, 2019

Related U.S. Application Data

(60) Provisional application No. 62/553,676, filed on Sep. 1, 2017.

(51) Int. Cl.
*G01N 33/68* (2006.01)
*G16B 20/00* (2019.01)
(Continued)

(52) U.S. Cl.
CPC ....... *G01N 33/6857* (2013.01); *G01N 33/564* (2013.01); *G01N 33/57415* (2013.01);
(Continued)

(58) Field of Classification Search
CPC .......... G01N 33/6857; G01N 33/6854; G01N 33/68; G01N 33/50; G01N 33/48; G16B 40/00; G16B 40/10
(Continued)

(56) References Cited

U.S. PATENT DOCUMENTS 7,031,845 B2   4/2006   Scott et al.
7,298,474 B2   11/2007  Drachev et al.
(Continued)

FOREIGN PATENT DOCUMENTS

AU   2008202217   6/2008
AU   2015100100   3/2015
(Continued)

OTHER PUBLICATIONS

International Application No. PCT/US2018/049256, International Search Report and Written Opinion dated Nov. 7, 2018.
(Continued)

*Primary Examiner* — Christine T Mui
(74) *Attorney, Agent, or Firm* — Squire Patton Boggs (US) LLP

(57) ABSTRACT

Provided herein are methods for identifying new biomarkers for various diseases using proteomics, peptidomics, metabolics, proteoglycomics, glvcomics, mass spectrometry and machine learning. The present disclosure also provides glycopeptides as biomarkers for various diseases such as cancer and autoimmune diseases.

17 Claims, 6 Drawing Sheets

(51) Int. Cl.
*G16B 40/00* (2019.01)
*G01N 33/564* (2006.01)
*G16B 40/20* (2019.01)
*G01N 33/574* (2006.01)
*G16B 40/10* (2019.01)

(52) U.S. Cl.
CPC ..... *G01N 33/6842* (2013.01); *G01N 33/6848* (2013.01); *G16B 20/00* (2019.02); *G16B 40/00* (2019.02); *G16B 40/10* (2019.02); *G16B 40/20* (2019.02); *G01N 2400/00* (2013.01); *G01N 2800/08* (2013.01)

(58) Field of Classification Search
USPC ...................................................... 436/173
See application file for complete search history.

(56) References Cited

U.S. PATENT DOCUMENTS

| | | |
|---|---|---|
| 8,163,896 B1 | 4/2012 | Bentwich et al. |
| 8,207,316 B1 | 6/2012 | Bentwich |
| 8,288,110 B2 | 10/2012 | Lopez et al. |
| 8,313,950 B2 | 11/2012 | Rovin et al. |
| 8,497,066 B2 | 7/2013 | Levenson et al. |
| 8,731,839 B2 | 5/2014 | Bhanot et al. |
| 8,921,053 B2 | 12/2014 | Siu et al. |
| 9,274,118 B2 | 3/2016 | Mansfield et al. |
| 9,335,331 B2 | 5/2016 | Lee et al. |
| 9,459,258 B2 | 10/2016 | Tang et al. |
| 9,846,158 B2 | 12/2017 | Mansfield et al. |
| 9,921,210 B2 | 3/2018 | Collins et al. |
| 9,968,666 B2 | 5/2018 | Lu et al. |
| 2004/0005634 A1 | 1/2004 | Patz et al. |
| 2004/0043436 A1 | 3/2004 | Vlahou et al. |
| 2004/0115774 A1 | 6/2004 | Kochendoerfer et al. |
| 2004/0229283 A1 | 11/2004 | Cygi et al. |
| 2005/0048547 A1 | 3/2005 | Zhao et al. |
| 2005/0260678 A1 | 11/2005 | Tomosugi et al. |
| 2005/0266576 A1 | 12/2005 | Soykan et al. |
| 2006/0053005 A1 | 3/2006 | Gulati et al. |
| 2006/0088894 A1 | 4/2006 | Wright et al. |
| 2006/0127950 A1* | 6/2006 | Bosques ................ G01N 33/66 435/7.1 |
| 2006/0141528 A1 | 6/2006 | Aebersold |
| 2006/0246495 A1 | 11/2006 | Garrett et al. |
| 2007/0054329 A1 | 3/2007 | Fung et al. |
| 2007/0077553 A1 | 4/2007 | Bentwich |
| 2007/0099251 A1 | 5/2007 | Zhang et al. |
| 2007/0111257 A1 | 5/2007 | Kohne |
| 2007/0202539 A1 | 8/2007 | Aebersold et al. |
| 2008/0026485 A1 | 1/2008 | Hueber et al. |
| 2008/0071148 A1 | 3/2008 | Bosques et al. |
| 2008/0118462 A1 | 5/2008 | Alani et al. |
| 2008/0132420 A1 | 6/2008 | Lubomirski et al. |
| 2008/0195570 A1 | 8/2008 | Alsafadi et al. |
| 2008/0261258 A1 | 10/2008 | Smith et al. |
| 2009/0035801 A1 | 2/2009 | Goldknopf et al. |
| 2009/0042229 A1 | 2/2009 | Folkman et al. |
| 2009/0053828 A1 | 2/2009 | Regnier |
| 2009/0104602 A1 | 4/2009 | Fernandez-Reyes et al. |
| 2009/0104603 A1 | 4/2009 | Satomaa et al. |
| 2009/0142332 A1 | 6/2009 | Ried et al. |
| 2009/0169576 A1 | 7/2009 | Crea et al. |
| 2009/0203055 A1 | 8/2009 | Ngantung et al. |
| 2009/0258848 A1 | 10/2009 | Chakravarti et al. |
| 2009/0317834 A1 | 12/2009 | Laine et al. |
| 2010/0017356 A1 | 1/2010 | Degrave et al. |
| 2010/0029006 A1 | 2/2010 | Rosenblatt et al. |
| 2010/0086948 A1 | 4/2010 | Gold et al. |
| 2010/0136700 A1 | 6/2010 | Bilello et al. |
| 2010/0240088 A1 | 9/2010 | Luider |
| 2010/0273661 A1 | 10/2010 | Qiu et al. |
| 2010/0280562 A1 | 11/2010 | Pi et al. |
| 2011/0136166 A1 | 6/2011 | Semmes et al. |
| 2011/0189680 A1 | 8/2011 | Keown et al. |
| 2011/0190151 A1 | 8/2011 | McManus et al. |
| 2011/0208433 A1 | 8/2011 | Grigorieva et al. |
| 2011/0212104 A1 | 9/2011 | Beaumont et al. |
| 2011/0224913 A1 | 9/2011 | Cui et al. |
| 2012/0028268 A1 | 2/2012 | Kentsis et al. |
| 2012/0053080 A1 | 3/2012 | Cui et al. |
| 2012/0122113 A1 | 5/2012 | Prions et al. |
| 2012/0149022 A1 | 6/2012 | Aw |
| 2012/0171694 A1 | 7/2012 | Mansfield et al. |
| 2012/0178642 A1 | 7/2012 | Salomon et al. |
| 2012/0264629 A1 | 10/2012 | Anderberg et al. |
| 2012/0283123 A1 | 11/2012 | Sarwal |
| 2013/0005598 A1 | 1/2013 | Haab et al. |
| 2013/0096023 A1 | 4/2013 | Rovin et al. |
| 2013/0115237 A1 | 5/2013 | Lu et al. |
| 2013/0158239 A1 | 6/2013 | Callewaert et al. |
| 2013/0203061 A1 | 8/2013 | Kuslich et al. |
| 2013/0261015 A1 | 10/2013 | Ahn et al. |
| 2013/0267439 A1 | 10/2013 | Mansfield et al. |
| 2013/0287801 A1 | 10/2013 | Castronovo |
| 2013/0288912 A1 | 10/2013 | Borrebaeck et al. |
| 2013/0316921 A1 | 11/2013 | Cohen et al. |
| 2014/0037658 A1* | 2/2014 | Nilsson ............... A61K 39/0007 424/184.1 |
| 2014/0080138 A1 | 3/2014 | Ralhan et al. |
| 2014/0148348 A1 | 5/2014 | Kuslich et al. |
| 2014/0162370 A1 | 6/2014 | Ling et al. |
| 2014/0322732 A1 | 10/2014 | Krek et al. |
| 2014/0343451 A1 | 11/2014 | Pannell et al. |
| 2014/0364341 A1 | 12/2014 | Mansfield et al. |
| 2015/0057169 A1 | 2/2015 | Siu et al. |
| 2015/0160233 A1 | 6/2015 | Tang et al. |
| 2015/0265687 A1 | 9/2015 | Geldhof et al. |
| 2015/0376723 A1 | 12/2015 | Keshavjee et al. |
| 2016/0003838 A1 | 1/2016 | Roedder et al. |
| 2016/0109437 A1 | 4/2016 | Cooper et al. |
| 2016/0146831 A1 | 5/2016 | Hueber et al. |
| 2016/0350477 A1 | 12/2016 | Mchugh |
| 2016/0369350 A1 | 12/2016 | Kassis |
| 2016/0370374 A1 | 12/2016 | Bosques et al. |
| 2017/0002095 A1 | 1/2017 | Satomaa et al. |
| 2017/0010265 A1 | 1/2017 | Kas et al. |
| 2017/0010269 A1 | 1/2017 | Pennington et al. |
| 2017/0016913 A1 | 1/2017 | Price et al. |
| 2017/0029888 A1 | 2/2017 | Cargill et al. |
| 2017/0030904 A1 | 2/2017 | Liu et al. |
| 2017/0161441 A1 | 6/2017 | Bilello |
| 2017/0176441 A1 | 6/2017 | Blume et al. |
| 2017/0205427 A1 | 7/2017 | West et al. |
| 2017/0247743 A1 | 8/2017 | Leung et al. |
| 2018/0003706 A1 | 1/2018 | Trenholm et al. |
| 2018/0017580 A1 | 1/2018 | Kaldate |
| 2018/0282376 A1 | 10/2018 | Alter et al. |
| 2019/0017117 A1 | 1/2019 | Barr et al. |
| 2019/0027249 A1 | 1/2019 | Fuksenko et al. |
| 2019/0072557 A1 | 3/2019 | Hill et al. |
| 2019/0113520 A1 | 4/2019 | Blume et al. |
| 2019/0131016 A1 | 5/2019 | Cohen et al. |

FOREIGN PATENT DOCUMENTS

| | | |
|---|---|---|
| CA | 2769406 | 2/2011 |
| CA | 2734535 | 3/2013 |
| CN | 100410663 C | 8/2008 |
| CN | 103278576 B | 12/2014 |
| EP | 1696237 A1 | 8/2006 |
| EP | 3035058 | 6/2016 |
| JP | 2009057337 A | 3/2009 |
| JP | 2009168646 A | 7/2009 |
| JP | 2014027898 A | 2/2014 |
| TW | I426269 B | 2/2014 |
| WO | WO 2006020269 A2 | 2/2006 |
| WO | WO 2007/144606 A2 | 12/2007 |
| WO | WO 2008/047086 A2 | 4/2008 |
| WO | WO 2008/108803 A2 | 9/2008 |
| WO | WO 2008/149088 A2 | 12/2008 |
| WO | WO 2009/075883 A2 | 6/2009 |
| WO | WO 2009/117666 A1 | 9/2009 |

(56) References Cited

FOREIGN PATENT DOCUMENTS

| WO | 2009138392 | 11/2009 |
|---|---|---|
| WO | WO 2010/144794 A1 | 12/2010 |
| WO | WO 2010/144797 A2 | 12/2010 |
| WO | WO 2012/016333 A1 | 2/2012 |
| WO | WO 2013/192530 A2 | 12/2013 |
| WO | 2015023068 | 2/2015 |
| WO | WO 2016/030888 A1 | 3/2016 |
| WO | WO 2016/036705 A1 | 3/2016 |
| WO | WO 2017/149300 A1 | 9/2017 |
| WO | WO 2017/190218 A1 | 11/2017 |
| WO | WO 2019/079639 A1 | 4/2019 |
| WO | WO 2020/160515 A1 | 8/2020 |

OTHER PUBLICATIONS

An et al., "Profiling of glycans in serum for the discovery of potential biomarkers for ovarian cancer", Journal of Proteome Research, American Chemical Society, vol. 5, No. 7, Jul. 1, 2006, pp. 1626-1635; XPO02449543.

Aoshima et al., "A simple peak detection and label-free quantitation algorithm for chromatography-mass spectrometry", BMC bioinformatics, 2014, 15(1):376; 14 pages.

Barroso et al., "Classification of congenital disorders of glycosylation based on analysis of transferrin glycopeptides by capillary liquid chromatography-mass spectrometry", Talanta (2016), 160, pp. 614-623; 10.1016/j.talanta.2016.07.055.

Cima et al., "Cancer genetics-guided discovery of serum biomarker signatures for diagnosis and prognosis of prostate cancer", Proceedings of the National Academy of Sciences of the United States of America, Feb. 22, 2011, vol. 108, No. 8, pp. 3342-3347; 10.1073/pnas.1013699108.

Datta et al., "Feature Selection and Machine Learning With Mass Spectrometry Data for Distinguishing Cancer and Non-Cancer Samples", Statistical Methodology, 2006, vol. 3, pp. 79-92.

Demichev et al., "DIA-NN: Neural networks and interference correction enable deep coverage in high-throughput proteomics", bioRxiv, Oct. 25, 2018, XP055696494, DOI: 10.1101/282699; Retrieved from the Internet: URL:https://www.biorxiv.org/content/10.11.

Eshghi et al., "Quality assessment and interference detection in targeted mass spectrometry data using machine learning", Clinical Proteomics, vol. 15, No. 33, Oct. 6, 2018, pp. 1-13.

Gallant et al., "Deconvolution of overlapping chromatographic peaks using a cerebellar model arithmetic computer neural network", Chemometrics and Intelligent Laboratory Systems, Elsevier Science Publishers B.V. Amsterdam, NL, vol. 18, No. 1, Jan. 1, 1993, pp. 41-57.

Geng et al., "Proteomics of glycoproteins based on affinity selection of glycopeptides from tryptic digests", Journal of Chromatography B, Mar. 10, 2001, vol. 752, pp. 293-306.

Geurts et al., "Proteomic Mass Spectra Classification Using Decision Tree Based Ensemble Methods", Bioinformatics, vol. 21, No. 15, pp. 3138-3145.

He et al., "Liquid chromatography mass spectrometry-based O-glycomics to evaluate glycosylation alterations in gastric cancer", Proteomics Clinical applications, Feb. 2016, vol. 10, pp. 206-215; doi:10.1002/prca.201500041.

Hilario et al., "Machine Learning Approaches to Lung Cancer Prediction From Mass Spectra", Proteomics, 2003, vol. 3, pp. 1716-1719; DOI 10.1002/pmic.200300523.

Hong et al., "Absolute Quantitation of Immunoglobulin G and Its Glycoforms Using Multiple Reaction Monitoring", Analytical Chemistry, Sep. 17, 2013, vol. 85, No. 18, doi:10.1021/ac4009995; 16 pages.

Imre et al., "Mass spectrometric and linear discriminant analysis of N-glycans of human serum alpha-1-acid glycoprotein in cancer patients and healthy individuals", Journal of Proteomics (2008), 71(2), pp. 186-197; 10.1016/j.jprot.2008.04.005.

Jeong et al., "Classification of core and outer fucosylation in N-glycoproteins by mass spectrometry with machine learning", Glycoconjugate Journal, Oct. 2017, vol. 34, Supp. Supplement 1, pp. S91-S92; 10.1007/s10719-017-9784-5.

Jinnelov et al., "Single-subunit oligosaccharyltransferases of Trypanosoma brucei display different and predictable peptide acceptor specificities", Journal of Biological Chemistry, 2017, 292(49), pp. 20328-20341; 10.1074/jbc.M117.810945.

Joenvaara et al., "Quantitative N-glycoproteomics reveals altered glycosylation levels of various plasma proteins in bloodstream infected patients", PLOS ONE, 2018, vol. 13, No. 3, pp. e0195006. Electronic Publication Date: Mar. 29, 2018; http://dx.doi.org/10.1371/journal.pone.0195006; 17 pages.

Ju et al., "Elevated level of serum glycoprotein bifucosylation and prognostic value in Chinese breast cancer", Glycobiology, 2016, vol. 26, No. 5, pp. 460-471; 10.1093/glycob/cwv117.

Kaji et al., "Lectin Affinity Capture, Isotope-Coded Tagging and Mass Spectrometry to Identify N-linked Glycoproteins", Nature Biotechnology, Jun. 2003 Jun., vol. 21(6), pp. 667-672.

Kiselyov et al, "VEGF/VEGFR signalling as a target for inhibiting angiogenesis", Expert Opin. Investig. Drugs, 2007, vol. 16, No. 1, pp. 83-107.

Kumozaki et al., "A Machine learning based approach to de novo sequencing of glycans from tandem mass spectrometry spectrum", IEEE/ACM Transactions on Computational Biology and Bioinformatics, Nov. 2015, vol. 12, No. 6, pp. 1267-1274; 10.1109/TCBB.2015.2430317.

Le et al., "Identification of Serum Amyloid A as a Biomarker to Distinguish Prostate Cancer Patients with Bone Lesions", Clinical Chemistry, vol. 51, Issue 4, Apr. 1, 2005, pp. 695-707.

Levner, "Feature Selection and Nearest Centroid Classification for Protein Mass Spectrometry", BMC Bioinformatics, 2005, vol. 6, No. 68, http://www.biomedcentral.com/1471-2105/6/68; 14 pages.

Li et al., "Site-Specific Glycosylation Quantitation of 50 Serum Glycoproteins Enhanced by Predictive Glycopeptidomics for Improved Disease Biomarker Discover", Analytical Chemistry, vol. 91, No. 8, Mar. 18, 2019, pp. 5433-5445; XP055689784.

Liang et al., "An adaptive workflow coupled with Random Forest algorithm to identify intact N-glycopeptides detected from mass spectrometry", Bioinformatics, 2014, 30(13), pp. 1908-1916; 10.1093/bioinformatics/btu139.

Liu et al., "Tandem $^{18}O$ Stable Isotope Labeling for Quantification of N-Glycoproteome", Journal of Proteome Research, vol. 9, No. 1, Jan. 4, 2010, pp. 227-236.

MacLean et al., "Skyline: an open source document editor for creating and analyzing targeted proteomics experiments", Bioinformatics, 26(7):966-968, 2010.

Neprasova et al., "Toward Noninvasive Diagnosis of IgA Nephropathy: A Pilot Urinary Metabolomic and Proteomic Study", Disease Markers, 2016, vol. 2016, Article ID 3650909, 10.1155/2016/3650909; 9 pages.

Noro et al., "Serum Aberrant N-Glycan Profile as a Marker Associated with Early Antibody-Mediated Rejection in Patients Receiving a Living Donor Kidney Transplant", Int. J. Molecular Sciences, Aug. 8, 2017, vol. 18, No. 8, 1731; doi:10.3390/ijms18081731.; 17 pages.

Tang et al., "Bioinformatics protocols in glycomics and glycoproteomics", Current Protocols in Protein Science, Apr. 2014, Computational Analysis, Supplement 76, pp. 2.15.1-2.15.7; DOI: 10.1002/0471140864.ps0215s76.

Tang et al., "Identification of N-Glycan Serum Markers Associated with Hepatocellular Carcinoma from Mass Spectrometry Data", Journal of Proteome Research, 2010, 9(1), pp. 104-112; 10.1021/pr900397n.

Thompson et al., "Tandem Mass Tags: A Novel Quantification Strategy for Comparative Analysis of Complex Protein Mixtures by MS/MS", Anal. Chem., Apr. 15, 2003, vol. 75(8), pp. 1895-1904; doi: 10.1021/ac0262560.

Tran et al., "Deep learning enables de novo peptide sequencing from data-independent-acquisition mass spectrometry", Nature Methods I https://doi.org/10.1038/s41592-018-0260-3, Published online: Dec. 20, 2018, vol. 16, No. 1, pp. 63-66.

(56) References Cited

OTHER PUBLICATIONS

Wang et al., "Integrative Analysis of Proteomic, Glycomic, and Metabolomic Data for Biomarker Discovery", IEEE Journal of Biomedical and Health Informatics, Sep. 2016, vol. 20, No. 5, pp. 1225-1231; doi: 1109/JBHI.2016.2574201.
Zhang et al., "Identification and quantification of N-linked glycoproteins using hydrazide chemistry, stable isotope labeling and mass spectrometry", Nature Biotechnology, Jun. 2003, vol. 21, No. 6, pp. 660-666.
Zohora et al., "DeepIso: A Deep Learning Model for Peptide Feature Detection from Lc-MS map", Scientific Reports, 2019, 9:171681 | https://doi.org/10.1038/s41598-019-52954-4.

\* cited by examiner

IDENTIFICATION AND USE OF GLYCOPEPTIDES AS BIOMARKERS FOR DIAGNOSIS AND TREATMENT MONITORING

CROSS-REFERENCE TO RELATED APPLICATIONS

This application claims priority to U.S. Provisional Patent Application No. 62/553,676, filed Sep. 1, 2017, which is incorporated by reference herein.

FIELD

The present disclosure relates generally to the field of multi-omics, in particular, glycomics and glycoproteomics, advanced instrumentation big data, machine learning and artificial intelligence to identify biomarkers for disease diagnosis and treatment monitoring.

BACKGROUND

Protein glycosylation and other post-translational modifications play vital structural and functional role in all aspects of human growth and development. Defective protein glycosylation accompanies several diseases. Identifying altered glycosylation at early disease stages provides opportunities for early detection, intervention and greater chance of survival in subjects affected. Currently, there are methods to identify biomarkers that can detect early cancer and discriminate a certain type of cancer from other diseases. Those methods include proteomics, peptidomics, metabolics, proteoglycomics and glvcomics using mass spectrometry (MS).

Although protein glycosylation provides useful information about cancer and other diseases, one drawback of the method is that the glycan cannot be traced back to the protein site of origin. To gain more knowledge about cancer biology and an early detection of cancer, it is important not only to identify the glycan, but also its site of attachment within the protein. Glycoprotein analysis is challenging in general due to several reasons. For example, a single glycan composition in a peptide may contain a large number of isomeric structures because of different glycosidic linkages, branching and many monosaccharides having the same mass. Further, the presence of multiple glycans that share the same peptide backbone causes the MS signal to split into various glycoforms, lowering their individual abundances compared to the peptides that are not glycosylated. Therefore, it has been challenging to develop algorithms that can identify glycans and their peptides from the tandem MS data. It is also challenging to obtain comprehensive fragmentation for both the glycan and the peptide as they have different fragmentation efficiencies.

Thus, there is a need to provide a method for site-specific glycoprotein analysis to obtain crucial and detailed information about protein glycosylation patterns that provide precise quantitative information about the glycosylation site heterogeneity in diseased cells, tissues or bio-fluids compared with the non-diseased ones. Such a method will lead to identify disease biomarkers, particularly for diseases such as cancer. There is also a need to reduce the time in identifying new biomarkers by combining the site-specific glycoprotein analysis data with deep learning and advanced LC/MS instrumentation to identify and validate new disease targets, such as glycan-based drug targets, for diseases such as cancer.

SUMMARY

The present disclosure relates to methods of identifying biomarkers for various diseases. The biomarkers are the glycosylated peptide fragments obtained via fragmentation of glycosylated proteins from biological samples. The methods of identifying the biomarkers rely upon the use of advanced mass spectrometry techniques that allow for the accurate mass measurements of the glycosylated peptide fragments as well as the site-specific glycosylation analysis. The mass spectroscopy methods of the present disclosure are advantageously useful in analyzing a large number of glycosylated proteins from the biological samples at a time.

In one embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments.

In another embodiment, the method comprises the subjects having a disease or a condition and subjects not having the disease or the condition. In a further embodiment, the subjects comprise subjects receiving a treatment for a disease or a condition and subjects having the disease or the condition but not receiving a treatment.

In another embodiment, the methods of the present disclosure are applicable to any disease or condition that can be detected by analyzing the glycosylated peptide fragments from the biological samples of a subject. In one embodiment, the disease is cancer. In another embodiment, the disease is an autoimmune disease. In another embodiment, the methods of the present disclosure provide glycosylated peptide fragments that are O-glycosylated or N-glycosylated. In another embodiment, the methods of the present disclosure provide glycosylated peptide fragments having an average length of from 5 to 50 amino acid residues.

In another embodiment, the methods of the present disclosure employ glycosylated proteins that are one or more of alpha-1-acid glycoprotein, alpha-1-antitrypsin, alpha-1B-glycoprotein, alpha-2-HS-glycoprotein, alpha-2-macroglobulin, antithrombin-III, apolipoprotein B-100, apolipoprotein D, apolipoprotein F, beta-2-glycoprotein 1, ceruloplasmin, fetuin, fibrinogen, immunoglobulin (Ig) A, IgG, IgM, haptoglobin, hemopexin, histidine-rich glycoprotein, kininogen-1, serotransferrin, transferrin, vitronectin and zinc-alpha-2-glycoprotein.

In another embodiment, the methods of the present disclosure comprise fragmentation of the glycosylated proteins using at least two proteases. In another embodiment, the methods of the present disclosure employ LC-MS techniques using multiple reaction monitoring mass spectrometry (MRM-MS).

In another embodiment, the present disclosure provides methods for identifying glycosylated peptide fragments as potential biomarkers for various diseases as described herein, wherein the biological sample is body tissue, saliva, tears, sputum, spinal fluid, urine, synovial fluid, whole blood, serum or plasma obtained from the subjects. In one embodiment, the subjects are mammals. In another embodiment, the subjects are humans.

In another embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments, wherein the machine learning approach is deep learning, neural network, linear discriminant analysis, quadratic discriminant analysis, support vector machine, random forest, nearest neighbor or a combination thereof. In another embodiment, the machine learning approach is deep learning, neural network or a combination thereof.

In another embodiment, the present disclosure provides methods for identifying glycosylated peptide fragments as potential biomarkers for various diseases as described herein, wherein the analysis further comprises genomic data, proteomics, metabolics, lipidomics data, or a combination thereof.

DETAILED DESCRIPTION

Definitions

Figure 1:
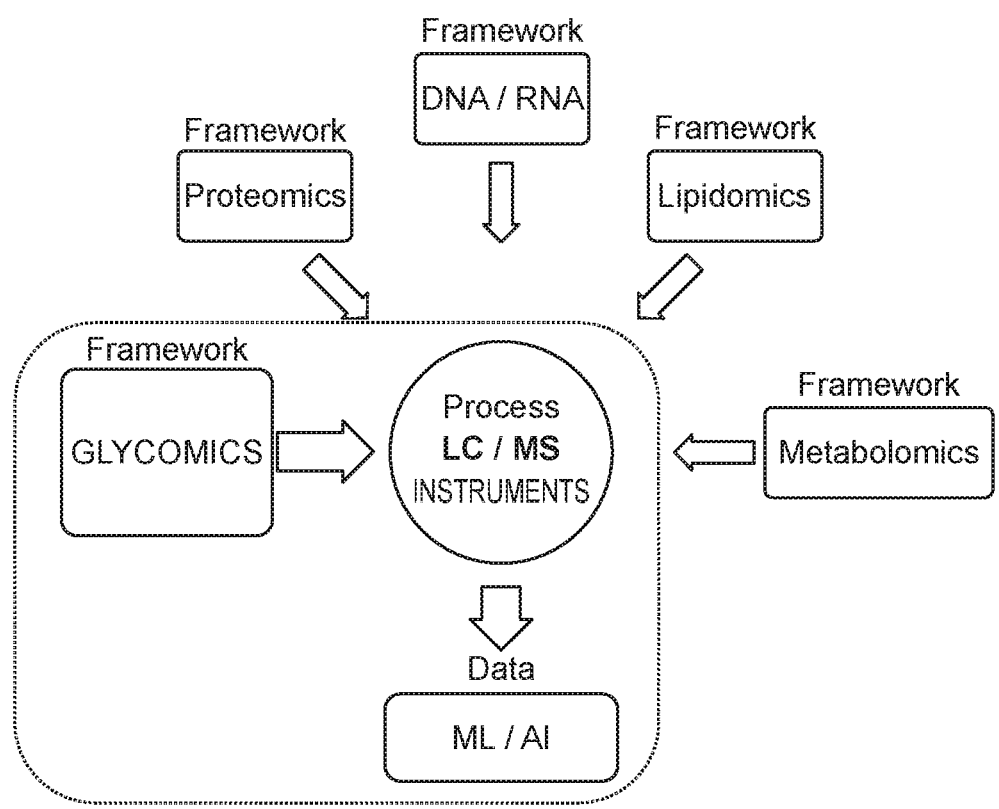
FIG. 1 is a Schematic diagram showing the integration of Glycomics, LC/MS and machine learning that can further be combined with protemomics, genomic, lipidomics and metabolics.

As used in the present specification, the following words and phrases are generally intended to have the meanings as set forth below, except to the extent that the context in which they are used indicates otherwise.

It is to be noted that as used herein and in the claims, the singular forms "a," "an" and "the" include plural referents unless the context clearly dictates otherwise.

The term "biological sample" refers to mean any biological fluid, cell, tissue, organ or a portion thereof. It also includes, but is not limited to, a tissue section obtained by biopsy, or cells that are placed in or adapted to tissue culture. It further includes, but is not limited to, saliva, tears, sputum, sweat, mucous, fecal material, gastric fluid, abdominal fluid, amniotic fluid, cyst fluid, peritoneal fluid, spinal fluid, urine, synovial fluid, whole blood, serum, plasma, pancreatic juice, breast milk, lung lavage, marrow, and the like.

The term "biomarker" refers to a distinctive biological or biologically-derived indicator of a process, event or a condition. A biomarker is also indicative of a certain biological state, such as presence of a disease or a condition or risk of a disease or a condition. It includes a biological molecule, or a fragment of a biological molecule, the change or detection of which can be correlated with a particular physical state or a condition. Example of biomarkers include, but are not limited to, biological molecules comprising nucleotides, amino acids, fatty acids, steroid, antibodies, hormones, steroids, peptides, proteins, carbohydrates, and the like. Further examples include glycosylated peptide fragments, lipoproteins, and the like.

The term "comprising" is intended to mean that the compositions and methods include the recited methods, but do not exclude others.

The term "glycan" refers to the carbohydrate portion of a glycoconjugate, such as a glycopeptide, glycoprotein, glycolipid or proteoglycan.

The term "glycoform" refers to a unique primary, secondary, tertiary and quaternary structure of a protein with an attached glycan of a specific structure.

The term "glycosylated peptide fragment" refers to a glycosylated peptide (or glycopeptide) having an amino acid sequence that is the same as part but not all of the amino acid sequence of the glycosylated protein from which the glycosylated peptide is obtained via fragmentation, e.g., with one or more proteases.

The term "multiple reaction monitoring mass spectrometry (MRM-MS)" refers to a highly sensitive and selective method for the targeted quantification of protein/peptide in biological samples. Unlike traditional mass spectrometry, MRM-MS is highly selective (targeted), allowing researchers to fine tune an instrument to specifically look for peptides/protein fragments of interest. MRM allows for greater sensitivity, specificity, speed and quantitation of peptides/protein fragments of interest, such as a potential biomarker. MRM-MS involves using a triple quadrupole (QQQ) mass spectrometer or quadrupole time-of-flight (qTOF) mass spectrometer.

The term "protease" refers to an enzyme that performs proteolysis or breakdown of proteins into smaller polypeptides or amino acids. Examples of a protease include, serine protease, threonine protease, cysteine protease, aspartate protease, glutamic acid protease, metalloprotease, asparagine peptide lyase and a combination thereof.

The term "subject" refers to a mammal. The non-liming examples of a mammal include a human, non-human primate, mouse, rat, dog, cat, horse, or cow, and the like. Mammals other than humans can be advantageously used as subjects that represent animal models of disease, pre-disease, or a pre-disease condition. A subject can be male or female. A subject can be one who has been previously identified as having a disease or a condition, and optionally has already undergone, or is undergoing, a therapeutic intervention for the disease or condition. Alternatively, a subject can also be one who has not been previously diagnosed as having a disease or a condition. For example, a subject can be one who exhibits one or more risk factors for a disease or a condition, or a subject who does not exhibit disease risk factors, or a subject who is asymptomatic for a disease or a condition. A subject can also be one who is suffering from or at risk of developing a disease or a condition.

The term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms.

Methods

The present disclosure, in some embodiments, relates to glycoproteomics glycoproteomics for biomarker discovery, target discovery and validation using advanced LC/MS instrumentation. The disclosure utilizes machine learning methods to process the molecular data. The analysis further comprises utilizing genomic data, proteomics, metabolics, lipidomics data, or a combination thereof in discovering new biomarkers for various diseases. The general schematic for the methods of this disclosure is shown in FIG. 1.

The present disclosure provides methods for site-specific glycosylation analysis that leads to identification of new types of biomarkers with higher sensitivity and specificity. The method comprises quantitation of glycosylated peptides, thus facilitating differential analysis of distinct glycoforms associated with specific proteins at distinct sites. The method provides information regarding the amount of protein and the site-specific glycosylation profile, thus providing insight into whether the altered glycosylation profile is due to the change in protein glycosylation or it is due to a change in protein concentration. The site specific glycosylation analysis in combination with machine learning method(s) provide identification of new biomarkers for various diseases or conditions.

The quantitative glycoproteomics methods of the disclosure are used to discover biomarkers of various diseases. The methods are based on the fact that specific glycoforms are elevated and others are down regulated in several diseases and the LC/MS methods of the present disclosure differentiate between the disease versus no disease by analyzing the significant glycosylation changes. In one embodiment, the site-specific glycosylation analysis comprises identifying the glycoproteins of interest, the sites of modification, what the modification is and then measuring the relative abundance of each modification. In some embodiments, the disease is cancer. In other embodiments, the disease is an autoimmune disease.

Using the methods of this disclosure, the biological samples from thousands of subjects are digitized to generate tremendous amount of data that undergoes deep machine learning analysis to discover new targets for various diseases. Specifically, deep learning is used to compare clustering of known and unknown peptides and their glycosylation signatures as seen by LC/MS in disease versus control states. Such discriminant analysis of the glycosylated peptides leads to the identification of the disease biomarkers.

The identification of the biomarkers and their corresponding features such as their expression level are then used for developing diagnostic test methods for a disease or a condition, wherein the methods rely upon, at least in part, on measuring one or more of the selected biomarkers and analyzing the result for an association with the disease or the condition. The methods can further be used in selecting one or more therapies, determining a treatment regimen or to monitor response to a therapy for the particular disease or condition. Thus, the present disclosure provides methods for prevention, diagnosis, therapy, monitoring and prognosis of a disease or a condition. In some embodiments, the methods are useful in discriminating between the subjects having a disease or a condition and healthy subjects. In some embodiments, the methods are useful in discriminating between subjects having cancer and healthy subjects. In some embodiments, the methods are useful in aiding the diagnosis of cancer or for monitoring cancer.

Targeted and Non-Targeted Approaches

The biomarker discovery methods of the present disclosure employ both targeted and/or non-targeted approaches. The methods typically comprise three different phases, namely, discovery phase, pre-validation phase and validation phase.

Discovery Phase

The targeted approach comprises identifying and monitoring the known glycoproteins with their known glycoforms in the biological samples of subjects. There are known FDA approved glycoprotein biomarkers for various diseases and those are monitored using the methods of this disclosure to identify the classification of the subjects. Typically, the glycosylation changes of the biomarkers are tumor-specific and are useful in identifying a possible risk of the disease or a disease stage. The targeted approach focuses on the known glycoproteins and their glycoforms that are chemically characterized and biologically annotated with the established biological importance at the start of the study before data acquisition is performed. Quantification is performed through the use of internal standards and authentic chemical standards.

Specifically, in the targeted approach, the site-specific glycosylation analysis is conducted in biological samples from case-control study of a number of subjects having a disease or condition and equal number of matched control subjects not having the disease or condition. The glycoprotein of interest, such as a disease related glycoprotein or a glycoprotein with a biological activity, is first identified in the biological sample. It is then analyzed using LC/MS for the site of modification, nature of modification, identity of the modification and the relative abundance of each modification, leading to identification and quantification of the peptide fragments. This approach uses triple quadrupole (QQQ) mass spectrometer for the quantification of the glycosylated peptide fragments which are then analyzed for its relation to the classification of the subjects.

The non-targeted approach comprises learning the glycosylation patterns of known as well as unknown peptide fragments to provide more information on changes in glycosylation patterns that is useful in identifying the classification of the subjects. The non-targeted approach is based on relative quantitation technique that provides "up or down regulation" of the glycoproteins. Specifically, the up or down regulation of the glycoproteins is monitored in relation to the classification of the subjects. For example, the glycoprotein fragments are monitored for subjects having a disease or a condition versus subjects not having a disease or a condition. This approach does not know the chemical identity of each glycoprotein fragment before the data is acquired. In one embodiment, the non-targeted approach uses quadrupole time-of-flight (qTOF) mass spectrometer for the analysis of the glycosylated peptide fragments. This approach involves using the instrumentation to accurately measure the mass of components in a sample, without any preconceived notion about what those components might be.

The candidates differently expressed between the groups (disease vs. no disease) are selected for further evaluation, using machine learning methods to allow for the prediction of classification with feature selection techniques with important clinical characteristics. Performance is evaluated using internal cross validation in which features are selected and models are constructed using the training set. The resulting models are evaluated on the test set that was not used in the construction of the model. The false positive rate is controlled by using the false discovery rate (FDR) approach introduced by Benjamin and Hochberg.

Pre-Validation Phase

The candidate biomarkers thus identified in the discovery phase are then tested in an independent test set of biological samples obtained from a number of subjects having a disease or a condition and their matched controls not having the disease or condition, to determine the performance of the candidate biomarkers. The selected biomarker, its ranking, together with any parameter estimation of the models developed in the discovery phase are all part of the modelling and are tested with this independent pre-validation phase. According to the signals of candidate biomarkers, a diagnostic test classifies the biological samples into two groups: those with a disease and those without a disease. The test is then assessed for its usefulness based on positive predictive value, negative predictive value, specificity and sensitivity. Also, the diagnostic performance is evaluated using receiver operating characteristic (ROC) curves to test which biomarkers or a combination of multiple biomarkers are statistically better diagnostic tests for a disease or condition. The individual biomarkers that are successfully validated are examined for subsequent inclusion to form a panel of composite markers. The composite markers are constructed by weighted multi-variable logistic regression or other classification algorithms.

Validation Phase

The candidate biomarkers retained in the pre-validation phase are then validated through independent validations using independent blinded biological samples from a number of subjects. The purpose of this phase is to assess the diagnostic precision of the selected biomarkers.

In one embodiment, the biomarker discovery method is applied to biological samples obtained from subjects having cancer. In some embodiments, biological samples from at least 20, at least 40, at least 60, at least 80 or at least 100 subjects are analyzed in each group (i.e. a group having cancer or a group not having cancer).

Both targeted and/or non-targeted approaches, along with the machine learning methods as described herein, provide new diagnostic methods for identifying possible risk and/or early stage detection of various diseases. In one embodiment, this disclosure provides the methods of identification of biomarkers that are based on the convergence of targeted and non-targeted approaches in combination with the machine learning method. The biomarkers identified by the methods of the present disclosure are useful in methods of diagnosis, methods of prognosis assessment, monitoring results of therapy, identifying subjects likely to respond to a particular treatment, drug screening, and the like.

In one embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments.

In another embodiment, the present disclosure provides the method as described herein, wherein subjects comprise subjects having a disease or condition and subjects not having the disease or condition. In a further embodiment, the subjects comprise subjects receiving a treatment for a disease and subjects having the disease but not receiving a treatment for the disease.

The methods of the present disclosure are applicable to any disease or condition that can be detected by analyzing the glycosylated peptide fragments from the biological samples of a subject. In one embodiment, the disease is cancer. In another embodiment, the cancer selected from breast cancer, cervical cancer or ovarian cancer. In another embodiment, the disease is an autoimmune disease. In another embodiment, the autoimmune disease is HIV, primary sclerosing cholangitis, primary biliary cirrhosis or psoriasis.

In another embodiment, the present disclosure provides the methods as described herein, wherein the glycosylated proteins are one or more of alpha-1-acid glycoprotein, alpha-1-antitrypsin, alpha-1B-glycoprotein, alpha-2-HS-glycoprotein, alpha-2-macroglobulin, antithrombin-III, apolipoprotein B-100, apolipoprotein D, apolipoprotein F, beta-2-glycoprotein 1, ceruloplasmin, fetuin, fibrinogen, immunoglobulin (Ig) A, IgG, IgM, haptoglobin, hemopexin, histidine-rich glycoprotein, kininogen-1, serotransferrin, transferrin, vitronectin and zinc-alpha-2-glycoprotein. In another embodiment, the glycosylated proteins are one or more of alpha-1-acid glycoprotein, immunoglobulin (Ig) A, IgG or IgM.

In another embodiment, the present disclosure provides the methods as described herein, wherein the glycosylated peptide fragment is N-glycosylated or O-glycosylated.

In another embodiment, the present disclosure provides the methods as described herein, wherein the glycosylated peptide fragments have an average length of from about 5 to about 50 amino acid residues. In some embodiments, the glycosylated peptide fragments have an average length of from about 5 to about 45, or from about 5 to about 40, or from about 5 to about 35, or from about 5 to about 30, or about from 5 to about 25, or from about 5 to about 20, or from about 5 to about 15, or from about 5 to about 10, or from about 10 to about 50, or from about 10 to about 45, or from about 10 to about 40, or from about 10 to about 35, or from about 10 to about 30, or from about 10 to about 25, or from about 10 to about 20, or from about 10 to about 15, or from about 15 to about 45, or from about 15 to about 40, or from about 15 to about 35, or from about 15 to about 30, or about from 15 to about 25 or from about 15 to about 20 amino acid residues. In one embodiment, the glycosylated peptide fragments have an average length of about 15 amino acid residues. In another embodiment, the glycosylated peptide fragments have an average length of about 10 amino acid residues. In another embodiment, the glycosylated peptide fragments have an average length of about 5 amino acid residues.

In another embodiment, the present disclosure provides the methods as described herein, wherein the one or more proteases comprise any protease that is used for fragmenting proteins. In one embodiment, the protease is a serine protease, threonine protease, cysteine protease, aspartate protease, glutamic acid protease, metalloprotease, asparagine peptide lyase or a combination thereof. A few representative examples of a protease include, but are not limited to, trypsin, chymotrypsin, endoproteinase, Asp-N, Arg-C, Glu-C, Lys-C, pepsin, thermolysin, ealastase, papain, proteinase K, subtilisin, clostripain, carboxypeptidase and the like. In another embodiment, the present disclosure provides the methods as described herein, wherein the one or more proteases comprise at least two proteases.

The methods of the present disclosure have several further applications. For example, the one of more biomarkers are useful to discriminate between the pre-disease state from a disease state, or a disease state from a normal state. Other non-disease specific health states can also be determined. For example, changes of the biomarker can be assayed at different times: in a subject with a disease, to monitor the progress of the disease; in a subject undergoing treatment, to monitor the effect of the treatment and in a subject post-treatment, to monitor a possible relapse. Also, the levels of a specific amount of biomarker also may allow for choosing the course of treatment of the disease. For example, a biological sample can be provided from a subject undergoing treatment regimens for a disease. Such treatment regimens can include, but are not limited to, exercise regimens, dietary supplementation, weight loss, surgical intervention, device implantation, and treatment with therapeutics or prophylactics used in subjects diagnosed or identified with a disease or condition.

Moreover, changes in glycopeptide ratios in a plurality of glycoproteins can be associated with a certain disease sate or absence of a disease. For example, presence of a plurality of particular glycopeptides in a biological sample may indicate absence of a disease, whereas presence of a plurality of other specific glycopeptides in a biological sample may indicate presence of the disease. Thus, various glycopeptide profiles or panels of glycopeptide biomarkers can be correlated with various states of a disease.

Figure 2:
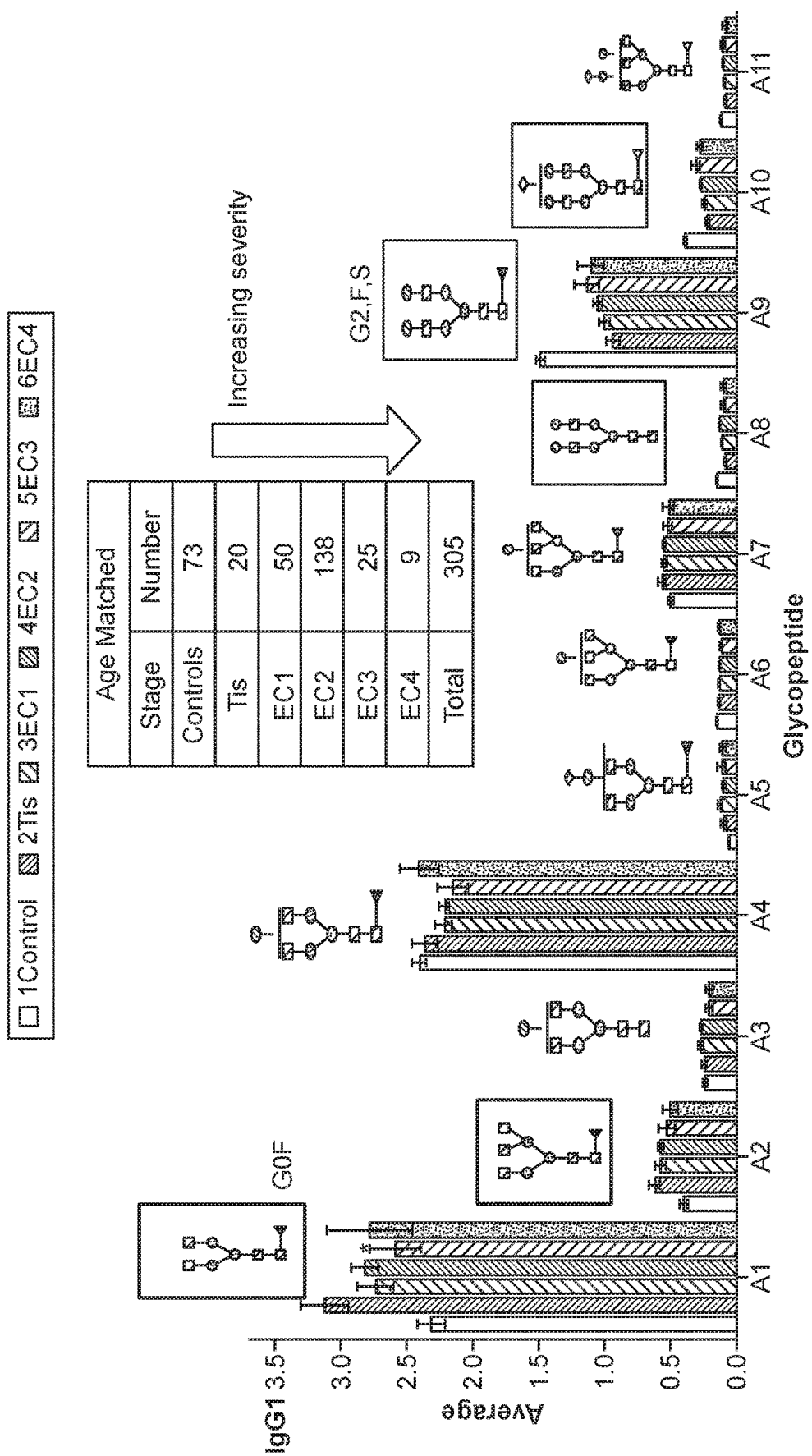
FIG. 2 shows changes in immunoglobulin G (IgG) glycopeptide ratios in plasma samples from breast cancer patients versus controls.

Example 2 shows quantitation results of changes in IgG1, IgG0 and IgG2 glycopeptides in plasma samples from breast cancer patients versus the controls. FIG. 2 illustrates that the levels of glycopeptides A1 and A2 were elevated as compared to the control, whereas the levels of glycopeptides A8, A9 and A10 were reduced as compared to the control in all stages of breast cancer studied in this experiment, thus indicating that glycopeptides A1, A2, A8, A9 and A10 are potential biomarkers for breast cancer.

Figure 3:
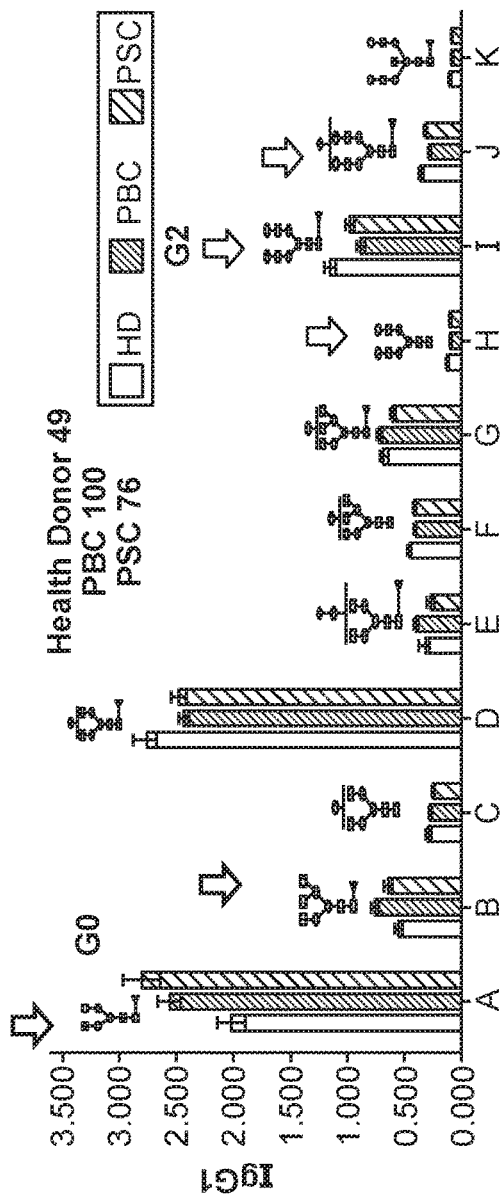
FIG. 3 shows changes in IgG glycopeptide ratios in plasma samples from primary sclerosing cholangitis (PSC) and primary biliary cirrhosis (PBC) samples versus healthy donors.
Figure 3:
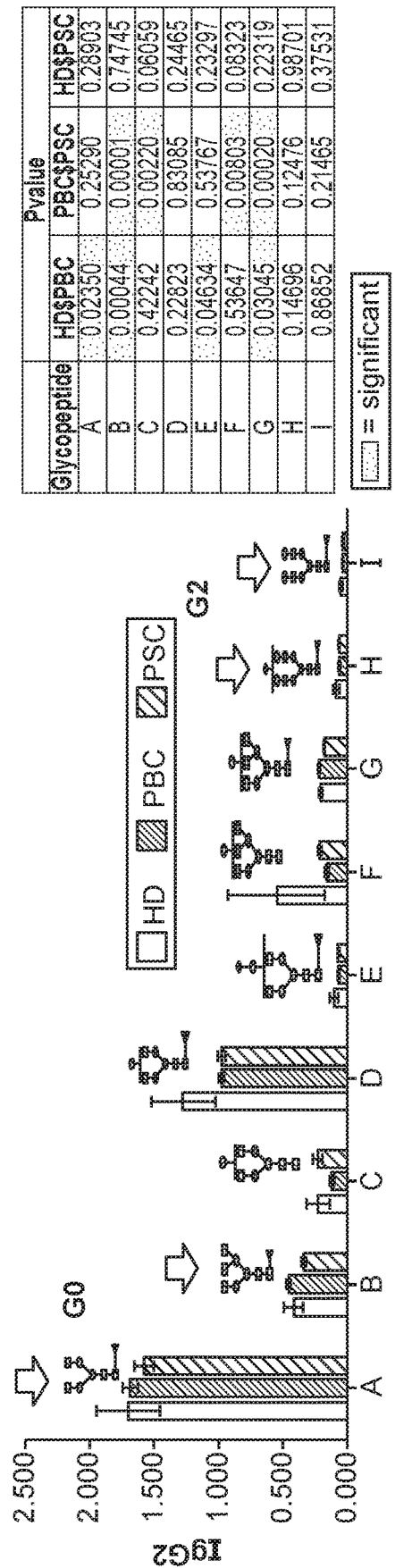
Figure 4:
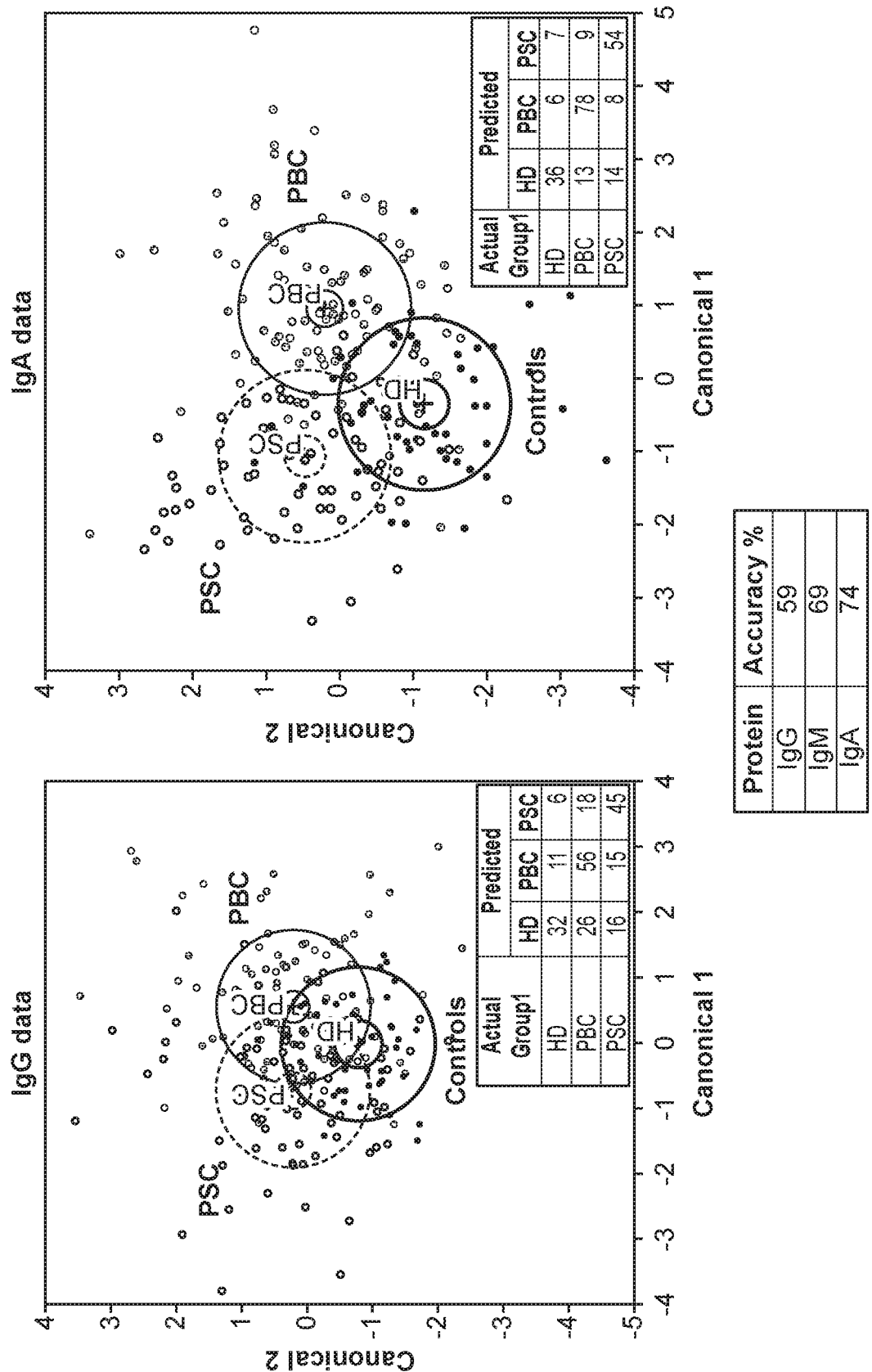
FIG. 4 shows the separate discriminant analysis data for IgG, IgA and IgM glycopeptides in plasma samples from PSC and PBC samples versus healthy donors.
Figure 4:
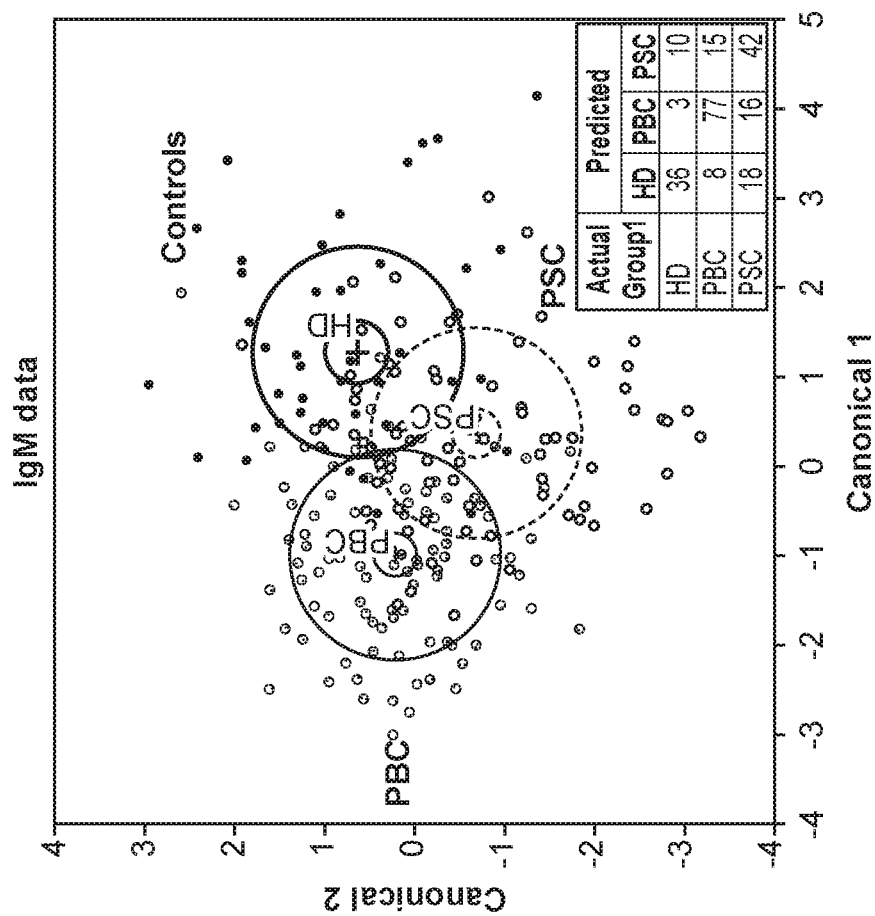

Example 3 shows quantification results of changes in IgG, IgM and IgA glycopeptides in plasma samples from patients having PSC and patients having PSC. FIG. 3 illustrates that glycopeptide A was elevated as compared to the healthy donors in plasma samples of patients having PBC and PSC, whereas glycopeptides H, I and J were reduced as compared to the healthy donors in plasma samples of patients having PBC and PSC. Thus, glycopeptides A, H, I and J are potential biomarkers for PBC and PSC. Further, the separate and combined discriminant analysis results are provided in FIG. 4 and FIG. 5 respectively indicating an accuracy of 88% for predicting the disease state in the combined discriminant analysis.

In some embodiments, the present disclosure provides methods, wherein the number of biomarkers that are detected and analyzed are 1, or more than 1, such as 2, 3, 4, 5, 6, 7, 8, 9, 10, 11, 12, 13, 14, 15, 16, 17, 18, 19 20, 21, 22, 23, 24, 25, 26, 27, 28, 30 or more. Thus, the disclosure also provides a panel of biomarkers that is useful in the diagnosis of a disease or condition.

Mass Spectroscopy

In one embodiment, the present disclosure provides methods as described herein that comprise quantitating the glycosylated peptide fragments by using a mass spectrometer. In one embodiment, the methods employ a technique called "multiple reaction monitoring (MRM)." This technique is often coupled with liquid chromatography (LC/MRM-MS) and allows the quantitation of hundreds of glycosylated peptide fragments (and their parent proteins) in a single LC/MRM-MS analysis. The advanced mass spectroscopy techniques of the present disclosure provide effective ion sources, higher resolution, faster separations and detectors with higher dynamic ranges that allow for broad untargeted measurements that also retain the benefits of targeted measurements.

The mass spectroscopy methods of the present disclosure are applicable to several glycosylated proteins at a time. For example, at least more than 50, or at least more than 60 or at least more than 70, or at least more than 80, or at least more than 90, or at least more than 100, or at least more than 110 or at least more than 120 glycosylated proteins can be analyzed at a time using the mass spectrometer.

In one embodiment, the mass spectroscopy methods of the present disclosure employ QQQ or qTOF mass spectrometer. In another embodiment, the mass spectroscopy methods of the present disclosure provide data with high mass accuracy of 10 ppm or better; or 5 ppm or better; or 2 ppm or better; or 1 ppm or better; or 0.5 ppm or better; or 0.2 ppm or better or 0.1 ppm or better at a resolving power of 5,000 or better; or 10,000 or better; or 25,000 or better; or 50,000 or better or 100,000 or better.

Biological Samples

The present disclosure provides methods that are based on quantitating the glycosylated peptide fragments from biological samples. In some embodiments, the biological samples are one or more clinical samples collected in the past, thus reducing the resources and time that must be committed to identifying new biomarkers. In some embodiments, the biological samples are from one or more past studies that occurred over a span of 1 to 50 years or more. In some embodiments, the studies are accompanied by various other clinical parameters and previously known information such as the subject's age, height, weight, ethnicity, medical history, and the like. Such additional information can be useful in associating the subject with a disease or a condition. In some embodiments, the biological samples are one or more clinical samples collected prospectively from the subjects.

In one embodiment, the present disclosure provides the methods as described herein, wherein the biological sample isolated from the subjects is one or more of saliva, tears, sputum, sweat, mucous, fecal material, gastric fluid, abdominal fluid, amniotic fluid, cyst fluid, peritoneal fluid, spinal fluid, urine, synovial fluid, whole blood, serum, plasma, pancreatic juice, breast milk, lung lavage, marrow. In another embodiment, the biological sample isolated from the subjects is body tissue, saliva, tears, sputum, spinal fluid, urine, synovial fluid, whole blood, serum or plasma. In another embodiment, the biological sample isolated from the subjects is whole blood, serum or plasma. In some embodiments, the subjects are mammals. In other embodiments, the subject are humans.

Diseases

The methods of the present disclosure are applicable to any disease or condition that can be detected by analyzing the glycosylated peptide fragments from the biological samples of a subject. In some embodiments, the disease or condition is cancer. In other embodiments, the cancer is acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, testicular cancer, thyroid cancer, urinary system cancer, uterine sarcoma, vaginal cancer, vascular system, Waldenstrom's macroglobulinemia, Wilms' tumor, and the like. In another embodiment, the cancer is breast cancer, cervical cancer or ovarian cancer.

In another embodiment, the disease is an autoimmune disease. In another embodiment, the autoimmune disease is acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune uticaria, autoimmune uveitis, Balo disease/Balo concentric sclerosis, Behcet's disease, Berger's disease, Bickerstaff's encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, glomerulonephritis, Goodpasture's syndrome, Graves' disease, Guillan-Barre syndrome, Hashimoto's encephalopathy, Hashimoto's thyroiditis, Henoch-Schonlein purpura, HIV, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonage-Turner syndrome, Pars planitis, pemphigus vulgaris, pernicious anemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjogren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis, and the like. In another embodiment, the autoimmune disease is HIV, primary sclerosing cholangitis, primary biliary cirrhosis or psoriasis.

Machine Learning

The biological samples are obtained from thousands of subjects which are then used for digitizing with the intention of deep mining for and validating previously undiscovered markers. In some embodiments, the biological samples are tumor samples or blood samples. They are digitized using LC/MS instruments to generate tremendous amount of data that undergoes deep machine learning analysis to discover new targets for various diseases. In some embodiments, the disease is cancer or autoimmune disease.

In one embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments, wherein the machine learning approach is deep learning, neural network, linear discriminant analysis, quadratic discriminant analysis, support vector machine, random forest, nearest neighbor or a combination thereof. In some embodiments, the machine learning approach is deep learning, neural network or a combination thereof. The analysis further comprises genomic data, proteomics, metabolics, lipidomics data, or a combination thereof. FIG. 1 displays a Schematic diagram showing the integration of Glycomics, LC/MS and machine learning that is further combined with protemomics, genomic, lipidomics and metabolics to identify the biomarkers for various diseases.

EXAMPLES

Example 1

General Method for Biomarker Discovery

In the targeted approach, the glycoprotein of interest, is first identified in the biological sample and then analyzed using LC/MS for the site of modification, nature of modification, identity of the modification and the relative abundance of each modification, leading to identification and quantification of the peptide fragments. This approach uses triple quadrupole (QQQ) mass spectrometer for the quantification of the glycosylated peptide fragments which is then analyzed for its relation to the classification of the subjects.

In the non-targeted approach, the glycosylation patterns of all peptide fragments (known as well as unknown) are analyzed to information on changes in glycosylation patterns in various subjects. Specifically, the up or down regulation of the glycoproteins is monitored in relation to the classification of the subjects. For example, the glycoprotein fragments are monitored for subjects having a disease or a condition versus subjects not having a disease or a condition. This approach uses quadrupole time-of-flight (qTOF) mass spectrometer for the analysis of the glycosylated peptide fragments.

Example 2

Quantification of IgG Glycopeptides as Potential Biomarkers for Breast Cancer

Plasma samples from breast cancer patients having various stages of cancer and their aged matched controls were analyzed for the IgG1, IgG0 and IgG2 glycopeptides and the changes in their ratios were compared. Specifically, 20 samples in Tis stage, 50 samples in EC1 stage, samples in EC2 stage, 25 samples in EC3 stage, 9 samples in EC4 stage and their 73 age matched control samples were subjected to MRM quantitative analysis on a QQQ mass spectrometer. As can be seen from the quantitative results in FIG. 2, the levels of certain IgG1 glycopeptides were elevated as compared to the controls, whereas the levels of certain IgG1 glycopeptides were reduced as compared to the controls in all stages of breast cancer studied in this experiment. See for example, IgG1 glycopeptides named as A1-A11, were monitored and it was found that the levels of glycopeptides A1 and A2 were elevated as compared to the control, whereas the levels of glycopeptides A8, A9 and A10 were reduced as compared to the control in all stages of breast cancer studied in this experiment. Thus, glycopeptides A1, A2, A8, A9 and A10 are potential biomarkers for breast cancer.

Example 3

Quantification of IgG Glycopeptides as Potential Biomarkers for PSC and PBC

Plasma samples from patients having primary sclerosing cholangitis (PSC), patients having primary biliary cirrhosis (PBC) and plasma samples from healthy donors were analyzed for IgG1 and IgG2 glycopeptides and the changes in their glycopepide ratios were compared. Specifically, 100 PBC plasma samples, 76 PSC plasma samples and plasma samples from 49 healthy donors were subjected to MRM quantitative analysis on a QQQ mass spectrometer. As can be seen from the quantitative results in FIG. 3, certain IgG1 glycopeptides were elevated as compared to the healthy donors, whereas certain IgG1 glycopeptides were reduced as compared to the controls in plasma samples of patients having PBC and PSC. See for example, glycopeptide A was elevated as compared to the healthy donors in patients having PBC and PSC, whereas glycopeptides H, I and J were reduced as compared to the healthy donors in plasma samples of patients having PBC and PSC. Thus, glycopeptides A, H, I and J are potential biomarkers for PBC and PSC.

Figure 5:
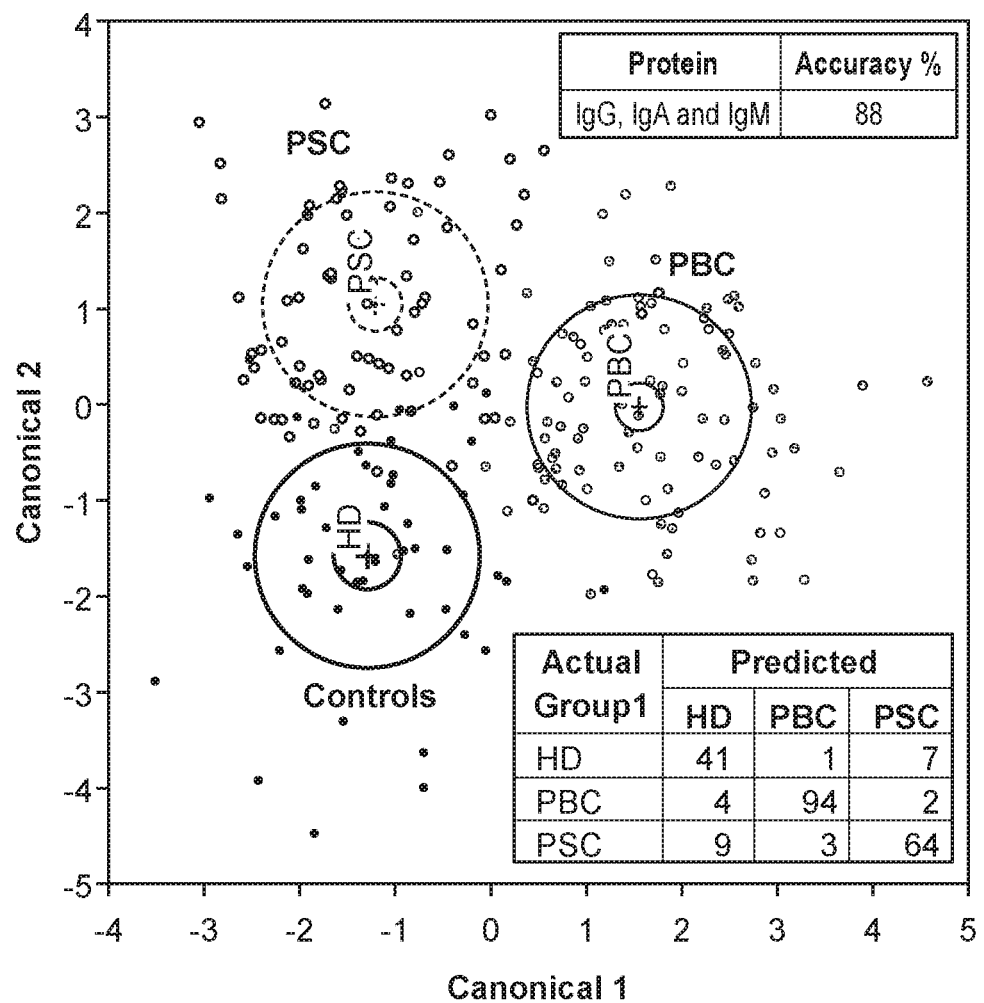
FIG. 5 shows the combined discriminant analysis data for IgG, IgA and IgM glycopeptides in plasma samples from PSC and PBC patients versus healthy donors.

Similar analysis was carried out on IgA and IgM glycoproteins in plasma samples of patients having PBC and plasma samples of patients having PSC. The discriminant analysis results are provided in FIG. 4 which indicate the % accuracy that can be predicted based on the separate data on IgG, IgM and IgA is 59%, 69% and 74% respectively. However, when the results are combined for all IgG, IgM and IgA, the discriminant analysis provides an accuracy of about 88% as shown in FIG. 5.

What is claimed is:

1. A method for identifying glycosylated peptide biomarkers, comprising:
    fragmenting glycosylated proteins using multiple reaction monitoring mass spectrometry (MRM-MS) in each of a plurality of biological samples isolated from subjects to produce glycosylated peptide fragments;
    wherein the MRM-MS is targeted on at least 50 or more glycosylated peptide fragments;
    quantitating the glycosylated peptide fragments to provide quantitation results;
    analyzing the quantitation results along with classification of the subjects with a machine learning method to select glycosylated peptide fragments useful for predicting the classification; and
    determining the identity of glycosylated peptide fragments;
    wherein the machine learning method is selected from deep learning, neural network, linear discriminant analysis, quadratic discriminant analysis, support vector machine, random forest, nearest neighbor, or a combination thereof; and
    wherein the machine learning method comprises combined discriminant analysis.

2. The method of claim 1, wherein the subjects comprise subjects having a disease or a condition and subjects not having the disease or the condition.

3. The method of claim 2, wherein the subjects comprise subjects receiving a treatment for a disease and subjects having the disease but not receiving a treatment.

4. The method of claim 3, wherein the disease is cancer or an autoimmune disease.

5. The method of claim 4, wherein the disease is cancer selected from breast cancer, cervical cancer and ovarian cancer.

6. The method of claim 5, wherein the disease is an autoimmune disease selected from HIV, primary sclerosing cholangitis, primary biliary cirrhosis and psoriasis.

7. The method of claim 1, wherein the glycosylated peptide fragment is N-glycosylated.

8. The method of claim 1, wherein the glycosylated peptide fragment is O-glycosylated.

9. The method of claim 1, wherein the glycosylated proteins are one or more of alpha-1-acid glycoprotein, alpha-1-antitrypsin, alpha-1B-glycoprotein, alpha-2-HS-glycoprotein, alpha-2-macroglobulin, antithrombin-III, apolipoprotein B-100, apolipoprotein D, apolipoprotein F, beta-2-glycoprotein 1, ceruloplasmin, fetuin, fibrinogen, immunoglobulin (Ig) A, IgG, IgM, haptoglobin, hemopexin, histidine-rich glycoprotein, kininogen-1, serotransferrin, transferrin, and vitronectin zinc-alpha-2-glycoprotein.

10. The method of claim 9, wherein the glycosylated proteins are one or more of alpha-1-acid glycoprotein, immunoglobulin (Ig) A, IgG and IgM.

11. The method of claim 1, wherein the glycosylated peptide fragments have an average length of from 5 to 50 amino acid residues.

12. The method of claim 1, wherein the biological sample is body tissue, saliva, tears, sputum, spinal fluid, urine, synovial fluid, whole blood, serum or plasma.

13. The method of claim 12, wherein the biological samples are whole blood, serum or plasma.

14. The method of claim 1, wherein the subjects are mammals.

15. The method of claim 14, wherein the subject are humans.

16. The method of claim 1, wherein the machine learning method comprises deep learning, neural network or a combination thereof.

17. The method of claim 1, wherein the analysis further comprises genomic data, proteomics, metabolics, lipidomics data, or a combination thereof.

* * * * *